United States Patent
Gowda et al.

(10) Patent No.: US 9,901,400 B2
(45) Date of Patent: Feb. 27, 2018

(54) STEREOTACTIC ACCESS DEVICES AND METHODS

(71) Applicant: Visualase, Inc., Minneapolis, MN (US)

(72) Inventors: Ashok Gowda, Bellaire, TX (US); Roger J. McNichols, Pearland, TX (US); Charles Houssiere, Houston, TX (US); Manish Ahuja, Pearland, TX (US); Ravish Patwardhan, New York, NY (US)

(73) Assignee: Visualise, Inc., Minneapolis, MN (US)

( * ) Notice: Subject to any disclaimer, the term of this patent is extended or adjusted under 35 U.S.C. 154(b) by 247 days.

(21) Appl. No.: 14/602,591

(22) Filed: Jan. 22, 2015

(65) Prior Publication Data
US 2015/0202011 A1 Jul. 23, 2015

Related U.S. Application Data

(60) Provisional application No. 61/930,781, filed on Jan. 23, 2014.

(51) Int. Cl.
*A61B 5/04* (2006.01)
*A61B 19/00* (2006.01)
(Continued)

(52) U.S. Cl.
CPC ........ *A61B 19/201* (2013.01); *A61B 17/3423* (2013.01); *A61B 90/11* (2016.02);
(Continued)

(58) Field of Classification Search
USPC .......................................... 600/424; 606/130
See application file for complete search history.

(56) References Cited

U.S. PATENT DOCUMENTS

| | | |
|---|---|---|
| 4,805,615 A | 2/1989 | Carol |
| 4,955,891 A | 9/1990 | Carol |

(Continued)

FOREIGN PATENT DOCUMENTS

| | | |
|---|---|---|
| JP | S6238147 A | 2/1987 |
| JP | D1342198 A | 2/2007 |

(Continued)

OTHER PUBLICATIONS

International Search Report and Written Opinion dated Apr. 23, 2015 for PCT/US2015/012675 claiming benefit of U.S. Appl. No. 14/602,591, filed Jan. 22, 2015 which claims priority from U.S. Appl. No. 61/930,781.

(Continued)

*Primary Examiner* — Nicole F Johnson
(74) *Attorney, Agent, or Firm* — Harness Dickey

(57) ABSTRACT

This invention is directed to devices and methods for stereotactic access, and particularly to a frameless stereotactic access device for accessing a body cavity and methods therefor. In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

28 Claims, 8 Drawing Sheets

(51) Int. Cl.
*A61B 17/34* (2006.01)
*A61B 90/11* (2016.01)
*A61B 90/10* (2016.01)
*A61B 90/00* (2016.01)

(52) U.S. Cl.
CPC . *A61B 2017/3407* (2013.01); *A61B 2090/103* (2016.02); *A61B 2090/3966* (2016.02); *A61B 2090/3983* (2016.02)

(56) References Cited

U.S. PATENT DOCUMENTS

| | | |
|---|---|---|
| 5,752,962 A | 5/1998 | D'Urso |
| 5,843,093 A | 12/1998 | Howard, III |
| 6,267,769 B1 | 7/2001 | Truwit |
| 6,327,491 B1 | 12/2001 | Franklin et al. |
| 6,491,699 B1 | 12/2002 | Henderson et al. |
| D556,153 S | 11/2007 | Burnside |
| 7,313,430 B2 | 12/2007 | Urquhart et al. |
| D612,479 S | 3/2010 | Zawackl et al. |
| D622,854 S | 8/2010 | Otto et al. |
| 7,794,469 B2 | 9/2010 | Kao et al. |
| 7,824,417 B2 | 11/2010 | Magnusson et al. |
| 7,947,022 B2 | 5/2011 | Amin et al. |
| 8,177,762 B2 | 5/2012 | Beasley et al. |
| 8,932,271 B2 | 1/2015 | Hamatake et al. |
| 2002/0038126 A1 | 3/2002 | Dominguez et al. |
| 2002/0049451 A1 | 4/2002 | Parmer et al. |
| 2004/0167542 A1 | 8/2004 | Solar et al. |
| 2005/0075649 A1 | 4/2005 | Bova et al. |
| 2005/0085719 A1 | 4/2005 | Franklin et al. |
| 2007/0016006 A1* | 1/2007 | Shachar ............. A61B 5/062 600/424 |
| 2010/0179564 A1 | 7/2010 | Mitchell et al. |
| 2010/0298830 A1 | 11/2010 | Browne et al. |
| 2011/0160621 A1 | 6/2011 | Nita |
| 2011/0190789 A1 | 8/2011 | Thiran et al. |
| 2011/0295271 A1* | 12/2011 | Kao ................. A61B 19/26 606/130 |
| 2013/0053867 A1* | 2/2013 | Gowda ............ A61B 17/00234 606/130 |
| 2015/0289992 A1 | 10/2015 | Anglin et al. |
| 2015/0320560 A1 | 11/2015 | Mulliken et al. |

FOREIGN PATENT DOCUMENTS

| | | |
|---|---|---|
| JP | D1356314 A | 1/2008 |
| JP | 2008526422 A | 7/2008 |
| WO | WO-95/13758 A1 | 5/1995 |
| WO | WO-2004021898 A1 | 3/2004 |
| WO | WO-04/107953 A2 | 12/2004 |
| WO | WO-05/046451 A2 | 5/2005 |
| WO | WO-2006075331 A2 | 7/2006 |
| WO | WO-09/060394 A1 | 5/2009 |
| WO | WO-2013028811 A1 | 2/2013 |
| WO | WO-2015112856 A1 | 7/2015 |

OTHER PUBLICATIONS

International Preliminary Report on Patentability dated Aug. 4, 2016 for PCT/US2015/012675 which claims benefit of U.S. Appl. No. 61/930,781, filed Jan. 23, 2014.
Japanese Office Action dated Jul. 28, 2017 in corresponding Japanese Application No. 2016-566859.
Supplemental Search Report for PCT/US2012/051949, European Application No. 12825002.4-1659 (publication No. 2779924) dated Jun. 19, 2015.
U.S. Appl. No. 29/480,423, filed Jan. 26, 2014.
U.S. Appl. No. 14/997,648, 2016-0193009, filed Jan. 18, 2016.

* cited by examiner

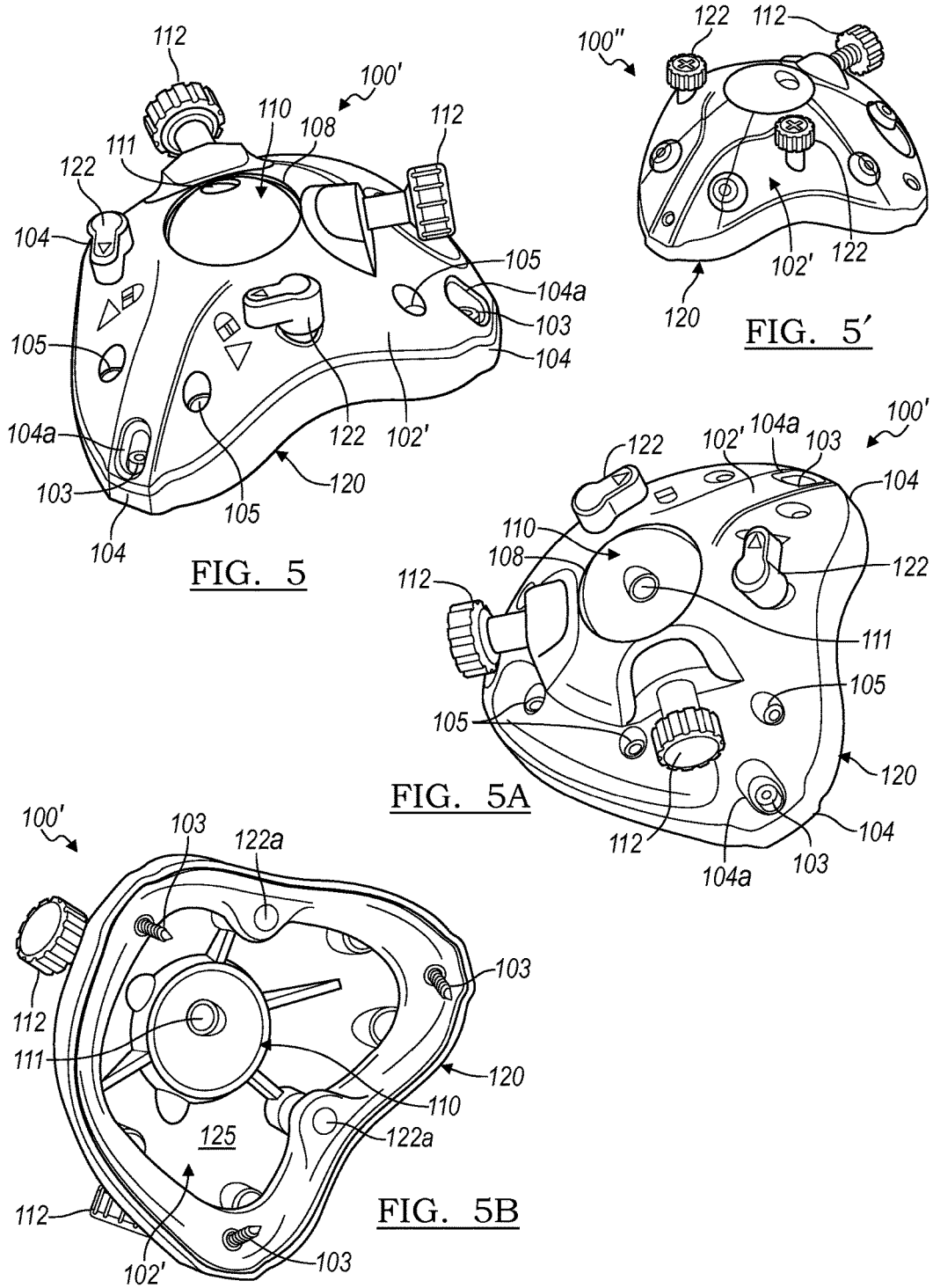

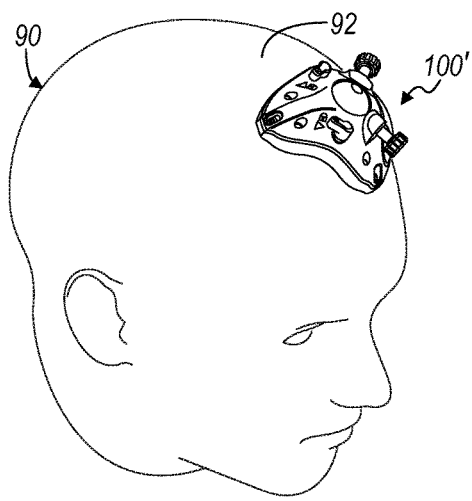
FIG. 6
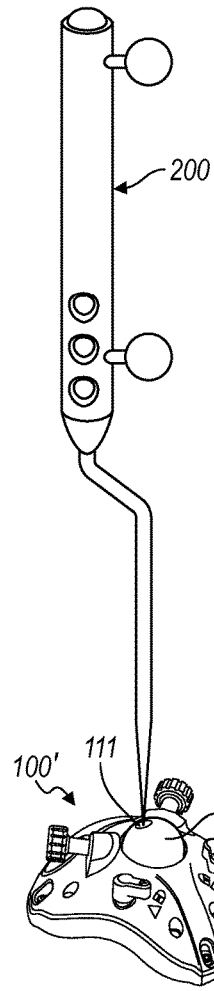
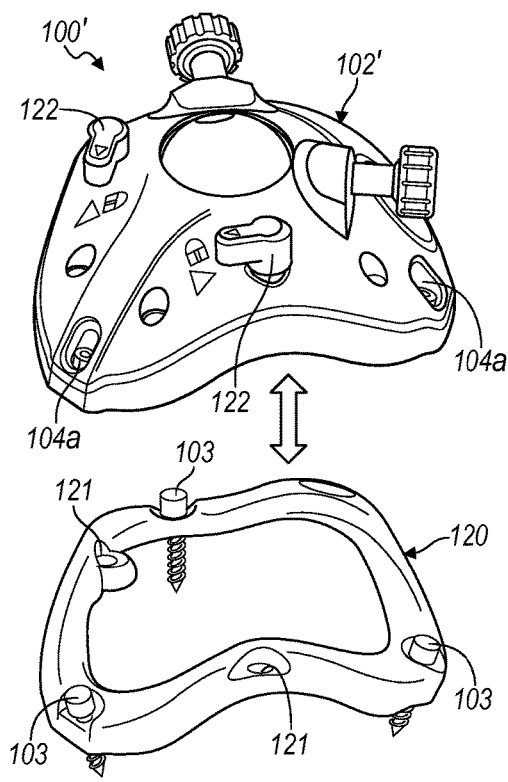
FIG. 6A
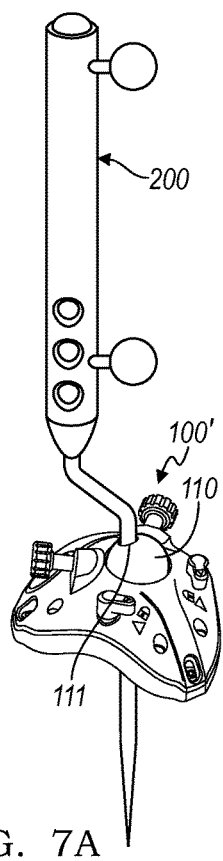
FIG. 7
FIG. 7A

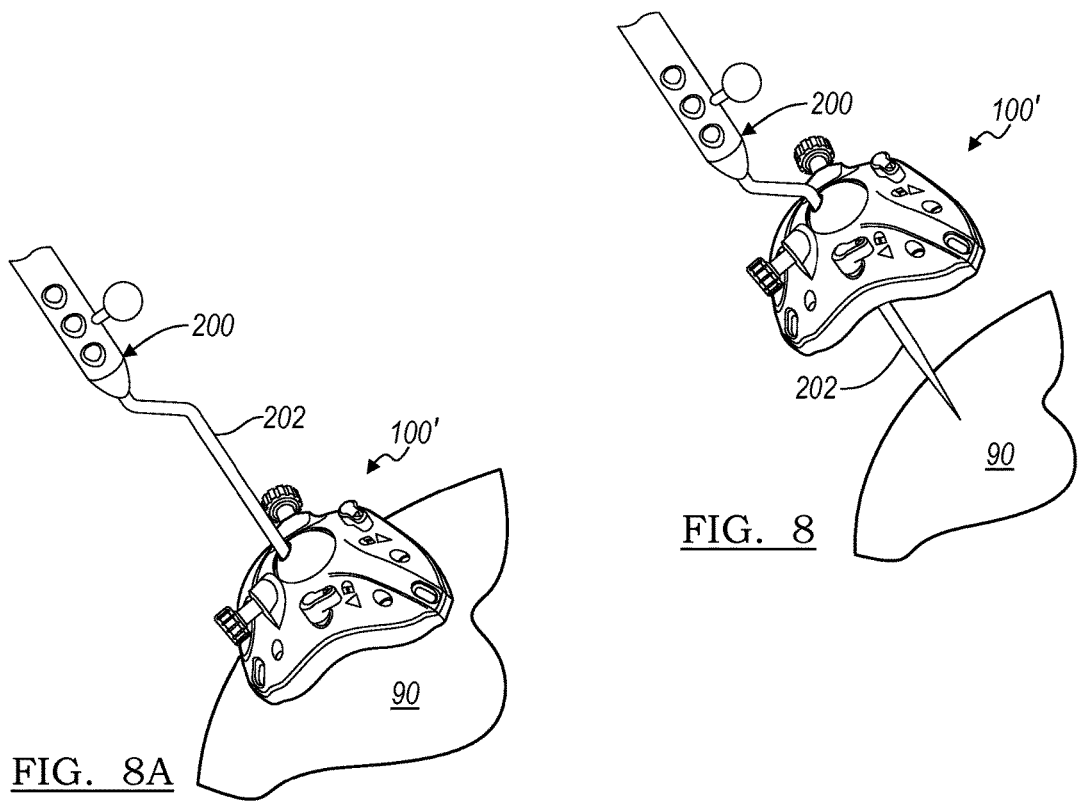
FIG. 8
FIG. 8A
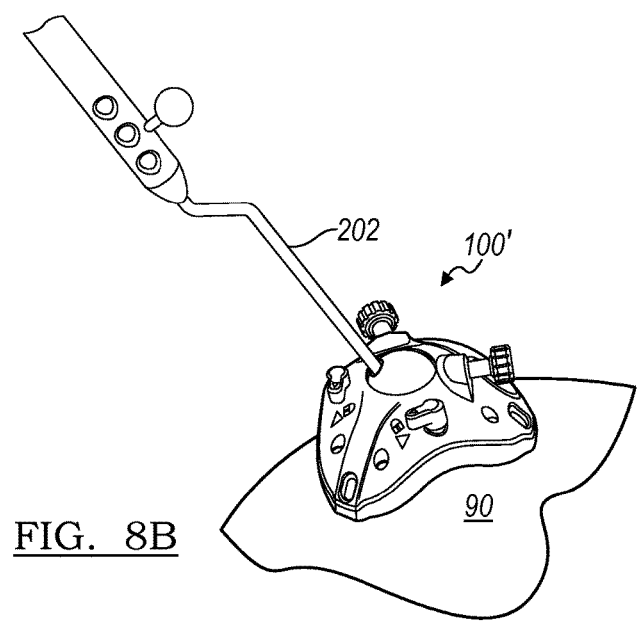
FIG. 8B

STEREOTACTIC ACCESS DEVICES AND METHODS

CROSS-REFERENCE TO RELATED APPLICATIONS

This application claims the benefit of U.S. Provisional Application No. 61/930,781 filed on Jan. 23, 2014. The entire disclosure of the above application is incorporated herein by reference.

FIELD

The present disclosure relates to devices and methods for stereotactic access, and particularly to a frameless stereotactic access device for accessing a body cavity and methods therefor.

BACKGROUND

This section provides background information related to the present disclosure which is not necessarily prior art.

Stereotactic head frames have a long and proven history in neurosurgery. The two most commonly used are the Leksell (Elekta) and CRW (Integra Neurosciences) frames. In these procedures, a frame is mounted to the head by screwing pins directly against the patient's skull for fixation at four points. The head with attached frame are then imaged by CT or MRI to identify targets, either manually or more frequently with computerized software, in relation to the external frame. Since both the frame and target can be viewed on the images, the distance of the target from given reference points on the frame can be measured in three coordinates. Next in the OR, an arc apparatus is attached to the head frame and adjusted based on the previously measured coordinates and desired trajectory. Once in position, a guide is used to drill a hole along a trajectory to the target. These head frames are associated with high accuracy (1-2 mm) for reaching target structures, much of which is achieved by having a permanent fixation between the skull and guide being used for creating the cranial access. Unfortunately, the frame is cumbersome, uncomfortable for patients, and time intensive.

Frameless stereotactic procedures rely on registration of the patient's skull using anatomical landmarks, skin fiducial, or bone fiducials to a pre-acquired MRI or CT scan. In the operating room the orientation of fiducial markers or skin surfaces is registered using stereoscopic cameras on the navigation system to a volume of brain images. Once registration is completed, the navigation system can show the relationship of any registered surgical instruments to patient's brain anatomy. The two major manufacturers of these neuronavigation systems are Medtronic and Brainlabs. Both companies offer accessories which attach to the patients bed to allow twist drill access to a target along a defined trajectory. A potential drawback to these accessories (Medtronic—Precision Aiming Device and Brainlab Varioguide) are that neither is directly attached to the patient's head, and therefore any movement of the drill may not be directly accompanied by a corresponding movement of the head. Both systems may also require additional time and resource to set up in the operating room. Finally, because skin fiducials are movable in relation to the underlying skull, additional error may be realized from the registration alone.

SUMMARY

This section provides a general summary of the disclosure, and is not a comprehensive disclosure of its full scope or all of its features.

This invention is directed to devices and methods for stereotactic access, and particularly to a frameless stereotactic access device for accessing a body cavity and methods therefor. In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

In one aspect, a stereotactic access device includes a plurality of mounting arms which may further include mounting devices or features such that, for example, the stereotactic access device may be mounted securely to a patient's body or part thereof. In some embodiments, the mounting arms may generally be adapted to provide a stable mounting of the stereotactic access device to a patient's body or part thereof. For example, many body parts have curved or irregular surfaces such that stable mounting may be desirable. In an exemplary embodiment, the mounting arms may form at least a stable plane such that when the mounting arms are attached to the patient's body, the stereotactic access device may generally be spatially stable and/or attached securely. In one embodiment, the stereotactic access device may include three mounting arms which may form a stable plane. The mounting arms may also be adapted to conform to the contours of a patient's body or part thereof, such as, for example, a skull. The mounting arms may further be adapted to contour, for example, such that there may be access space between the stereotactic access device and the patient's body and/or portion thereof. This may be desirable, for example, to manipulate a medical device and/or other device between the stereotactic access device and the patient's body and/or portion thereof.

In another aspect, a stereotactic access device includes a mounting and/or guiding feature such that a medical device and/or other device may be mounted to or guided to the stereotactic access device such that, for example, the device may be retained at a particular orientation and/or spatial relationship to the patient's body or part thereof. In some embodiments, the mounting and/or guiding feature may include a rotatable portion, such as an orbitally rotatable and/or swivelable portion, such that the orientation of the portion may be changed with respect to the patient's body, a portion thereof, and/or the rest of the stereotactic access device. In an exemplary embodiment, the mounting and/or guiding feature may include, for example, a rotating sphere which may further include a guide channel to, for example, receive a medical device and/or other device. The stereotactic access device may further include a locking and/or fixing feature for reversibly locking the orientation and/or position of the mounting and/or guiding feature relative to the stereotactic access device. For example, at least one securing screw may be utilized to frictionally contact and/or at least partially screw into a mounting and/or guiding feature to lock its position and/or orientation. Also for example, at least two securing screws may be utilized with mounting and/or guiding features having multiple degrees of freedom to aid in preventing loss of alignment and orientation, such as by each locking a particular axis of rotation.

In some embodiments, the mounting and/or guiding feature may include a centered channel, and in other embodiments, the mounting and/or guiding feature may include an off-center channel and/or multiple channels such that a greater degree of variability in position and trajectory for guiding a medical device and/or other device through the stereotactic access device may be achieved from a single static mounting of the stereotactic access device onto a patient's body. This variability may be desirable as unexpected and/or unplanned obstructions may be present in a planned trajectory to a target and it may generally be desirable to make small adjustments to the trajectory without having to reposition the entire stereotactic access device which may be attached a patient's body.

In a further aspect, a stereotactic access device includes features for aiding in mounting, positioning and/or registering the position and/or orientation of the stereotactic access device, for example, in relation to the patient's body and/or portion thereof. In some embodiments, the stereotactic access device may include, for example, mounting hardware such as, for example, screws, nails, bolts, pins, and/or any other appropriate mounting hardware or combination thereof. For certain curvatures and/or shapes of a body and/or portion thereof, spacers and/or other adjustment accessories, such as spacers between the end of the mounting arm(s) and the body, may be utilized such that a stable plane may be established with the stereotactic access device. In general, the mounting hardware may provide, for example, stable and/or secure retention and/or fixation of the stereotactic access device to a patient's body and/or portion thereof, such as, for example, to a bone or soft tissue via, for example, mounting arms. In some embodiments, the mounting hardware may also provide and/or act as, for example, fiducial markers for aiding in positioning and/or registering the position and/or orientation of the stereotactic access device, such as, for example, relative to the patient's body and/or portion thereof. For example, the mounting hardware may be registered and/or imaged by a detection modality, such as, for example, magnetic resonance imaging (MRI), X-ray, computerized tomography (CT), ultrasound, and/or any other appropriate detection modality or combination thereof.

In another aspect, a stereotactic access device is utilized in methods for accessing the interior of a patient's body at a particular location and/or along a particular trajectory. In an exemplary embodiment, a method for stereotactic access may include:

Step 1: After registration of the patient and navigation tools, a standard navigation wand may be used to determine and mark a rough entry point, and the patient may then be prepped. The navigation wand may then be inserted into the sphere of the stereotactic access device such that the surgeon may hold both devices, for example, with one hand.

Step 2: Using stereotactic navigation software, the surgeon may find the desired entry point again and may then align the navigation wand with the planned trajectory to a target. The surgeon may then slide the stereotactic access device down onto the patient's body and mounting hardware, such as, for example, three small titanium screws, may then be secured, for example, through the skin and into bone, such as, for example, the skull. The wand may be used again to confirm the trajectory, such as prior to locking the device in place.

Step 3: The surgeon may then remove the navigation wand and replace it with, for example, one of several various sized drill adapters. A stab incision may also be made at the entry site under the stereotactic access device. A surgical drill may then be inserted along the locked trajectory and a twist drill hole may be created through, for example, a bone such as the skull.

Step 4: The drill adapter may then be retracted to optionally allow, for example, a bone screw or anchor to be placed under the stereotactic access device. The drill adapter may be made to fit into the bone screw or anchor's proximal end such that the threads of the screw may fall into the hole created in step 3. A biopsy probe may also be passed directly through an appropriate adapter, for example, such as with its own thumb screw, and may be used to acquire, for example, tissue samples.

Step 5: For placement of probes or electrodes, the surgeon may secure the bone screw by securing it in, for example, the previously drilled hole.

Step 6: The stereotactic access device may be removed, for example, by unscrewing the three screws, and if any stab incisions were created, they may be closed using a single staple or suture. A Touhy-Borst adapter may also be threaded onto the proximal female luer of the bone screw, which may allow applicators to pass through while ensuring a sterile field.

In some embodiments, the stereotactic access device may also be left in place after a hole is drilled. For example, a bone screw may connect to the stereotactic access device such that a continuous sealed channel may be established from the stereotactic access device through the bone screw and into the body. A sealing cap and/or other sealing component may also be included to close off the introducing end of the stereotactic access device.

In other embodiments, the stereotactic access device may be left in place and an introducer may be inserted into the channel of the stereotactic access device and into the drilled hole in the body. The end of the introducer may further include a cap and/or a seal such that the channel may be kept sterile.

In some aspects, the stereotactic access device may be desirable as it may generally be utilized with existing and/or standard practice navigation devices, probes and/or systems, and may thus be adaptable to a diverse number of medical practices with very little additional training and/or the need for specialized equipment. For example, the stereotactic access device may generally be compatible and/or be compatible via adapters to receive a standard navigation probe or wand, treatment devices, drills and/or other equipment used in stereotactic surgery. Further, use of the stereotactic access device may generally be intuitive and aid in surgical usage with a minimal number of moving parts and/or components such that, for example, users may use the stereotactic access device with minimal difficulty, while still being highly versatile in application due to a universal use design.

In an exemplary aspect, a stereotactic access device may be a multiple part device which may, for example, be utilized to aid in maintaining a sterile field for use in stereotactic surgery while establishing a trajectory to a target inside a patient's body. In one exemplary embodiment, the stereotactic access device may include a frame portion and an attachable/detachable cover portion, such that the frame portion may be secured to the patient's body, while the cover portion may be attached and removed from the frame portion. This may be desirable as the stereotactic procedures may take place partially in a sterile environment, such as an operating room, and partially in an unsterile environment, such as a medical imaging room or suite. Thus, prior to performing a stereotactic surgical procedure, the stereotactic access device may be oriented and attached to a patient's body in an unsterile environment using the frame portion and an unsterile cover portion, followed by removal of the unsterile cover portion and replacement with a sterile cover portion for use in a sterile environment.

In some embodiments, the cover portion(s) may also include additional fiducial markers, as discussed above, such that they may aid in providing additional registration information and may also be used to verify proper alignment and attachment of the cover portion(s) to the frame portion as they are removable.

In some embodiments, the cover portion(s) and the frame portion may include features for reversible secure attachment to each other, which may include, but are not limited to, screws, nuts, bolts, nails, magnets, reversible adhesives, locking levers, and/or any other appropriate reversible secure attachments.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIGS. 2-1, 2-2, 2-3, 2-4, 2-5 and 2-6 illustrate the steps of a method of stereotactic access to a patient's body in some embodiments of the present invention;

FIGS. 3 and 3A illustrate an example of a frameless stereotactic access device;

FIGS. 4, 4A and 4B illustrate a frameless stereotactic access device with a sealed device introducer;

FIGS. 5, 5A and 5B illustrate a frameless stereotactic access device with a cover portion and a frame portion;

FIG. 5' illustrates a frameless stereotactic access device with a cover portion and a frame portion with a single securing screw for the mounting ball;

FIG. 6 shows a frameless stereotactic access device attached to a patient's body;

FIG. 6A shows a frameless stereotactic access device with reversibly attachable cover portion and frame portion;

FIGS. 7, 7A, 8, 8A, 8 B, 8C, 8D, and 8E illustrate an example of aligning and securing a frameless stereotactic access device to a patient's body.

Corresponding reference numerals indicate corresponding parts throughout the several views of the drawings.

DETAILED DESCRIPTION

Figure 1:
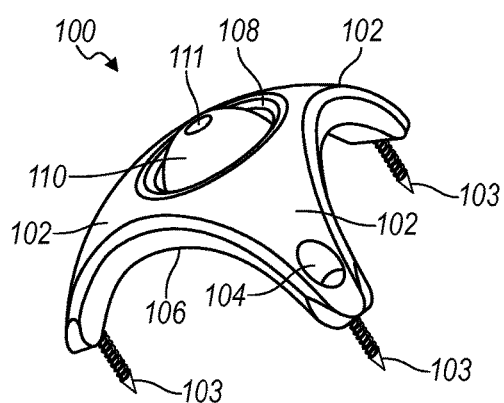
FIGS. 1, 1A, 1B and 1C illustrate a stereotactic access device in some embodiments of the present invention.

Example embodiments will now be described more fully with reference to the accompanying drawings.

The detailed description set forth below is intended as a description of the presently exemplified devices, methods and materials provided in accordance with aspects of the present invention, and it is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

This invention is directed to devices and methods for stereotactic access, and particularly to a frameless stereotactic access device for accessing a body cavity and methods therefor. In general, a stereotactic device may include portions or features for fixing the device to a portion of a patient's body, such as, for example, a skull, such that the device may be generally spatially fixed in relation to the patient's body or part thereof. The stereotactic device may also generally include portions or features for guiding a medical device or other device at a particular trajectory in relation to the patient's body or part thereof.

In one aspect, a stereotactic access device includes a plurality of mounting arms which may further include mounting devices or features such that, for example, the stereotactic access device may be mounted securely to a patient's body or part thereof. In some embodiments, the mounting arms may generally be adapted to provide a stable mounting of the stereotactic access device to a patient's body or part thereof. For example, many body parts have curved or irregular surfaces such that stable mounting may be desirable. In an exemplary embodiment, the mounting arms may form at least a stable plane such that when the mounting arms are attached to the patient's body, the stereotactic access device may generally be spatially stable and/or attached securely. In one embodiment, the stereotactic access device may include three mounting arms which may form a stable plane. The mounting arms may also be adapted to conform to the contours of a patient's body or part thereof, such as, for example, a skull. The mounting arms may further be adapted to contour, for example, such that there may be access space between the stereotactic access device and the patient's body and/or portion thereof. This may be desirable, for example, to manipulate a medical device and/or other device between the stereotactic access device and the patient's body and/or portion thereof.

FIG. 1 illustrates an example of an embodiment of a stereotactic access device 100. In some embodiments, such as illustrated, the stereotactic access device 100 may generally be a tripod and may include mounting arms 102, such as the three illustrated, which may provide a stable planar platform when mounted to a patient's body. The mounting arms 102 may also generally form a space 106 between the stereotactic access device 100 and a patient's body. This may be desirable such that the area may be freely accessed when the stereotactic access device 100 is in place on the patient's body.

In another aspect, a stereotactic access device includes a mounting and/or guiding feature such that a medical device and/or other device may be mounted to or guided to the stereotactic access device such that, for example, the device may be retained at a particular orientation and/or spatial relationship to the patient's body or part thereof. In some embodiments, the mounting and/or guiding feature may include a rotatable portion such that the orientation of the portion may be changed with respect to the patient's body, a portion thereof, and/or the rest of the stereotactic access device. In an exemplary embodiment, the mounting and/or guiding feature may include, for example, a rotating sphere which may further include a guide channel to, for example, receive a medical device and/or other device. Various adapters, shims and/or other devices may be utilized to accommodate different sized and/or shaped devices securely in the guide channel.

In FIG. 1, the stereotactic access device 100 may include a mounting ball 110, which may be retained in track 108. The mounting ball 110 may generally rotate in the track 108 such that the guide channel 111 may be aligned at the appropriate angle, such as illustrated in FIG. 1A. The mounting ball 100 may thus retain another device, such as, for example, a navigation wand 200, relative to the patient's body 90, such as illustrated in FIG. 1A. The mounting ball 110 may also include a securing part or feature, such as, for example, a securing screw, such that the mounting ball 110 may be locked in a particular orientation, such as with the thumbscrew 112 illustrated in FIGS. 1B and 1C. The thumbscrew 112 can include a distal pointed tip that enables the thumbscrew 112 to bite into the ball 110 in order to securely hold the ball 110 in place. For example, the tip of the thumbscrew 112 can be configured as a self-tapping screw tip.

Figure 1B:
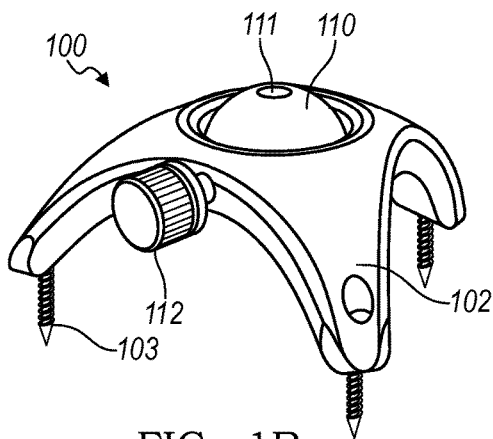
Figure 1A:
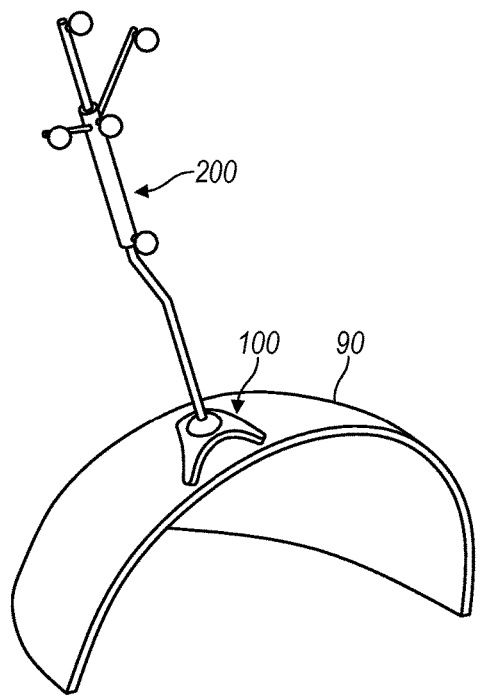
Figure 1C:
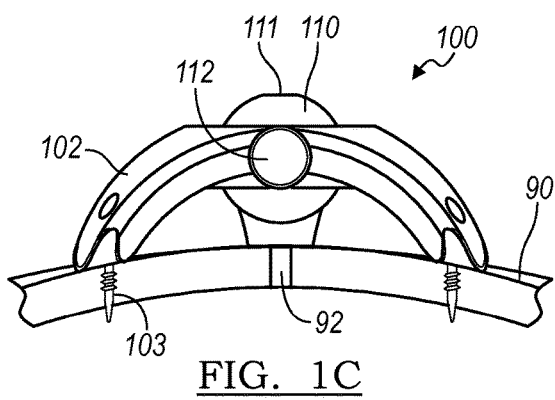
Figures 1, 2:
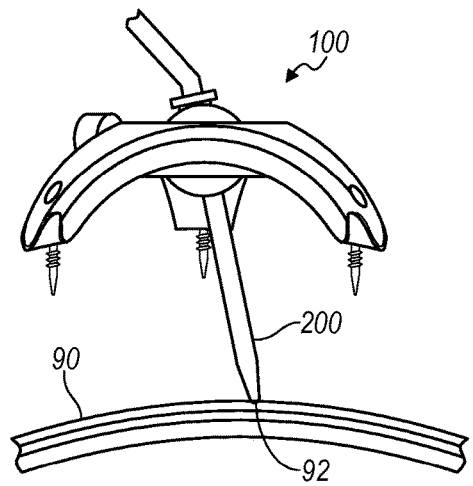
Figure 2:
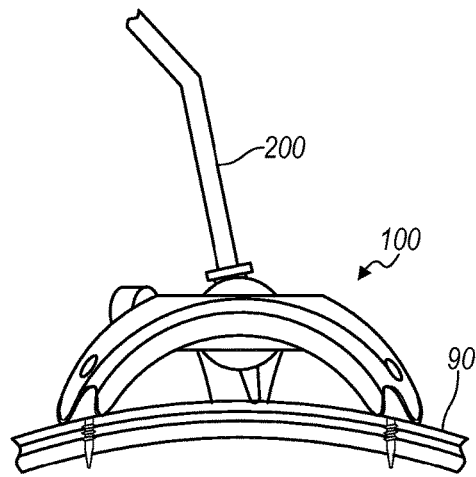
Figures 2, 3:
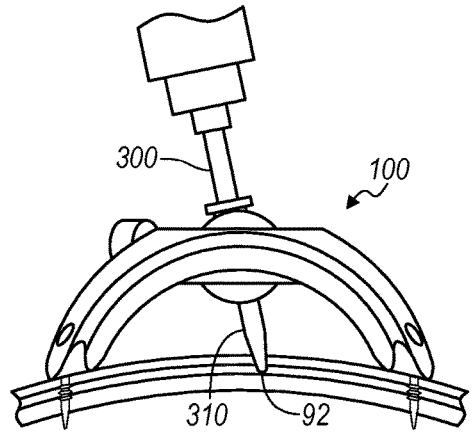
Figures 2, 3, 4:
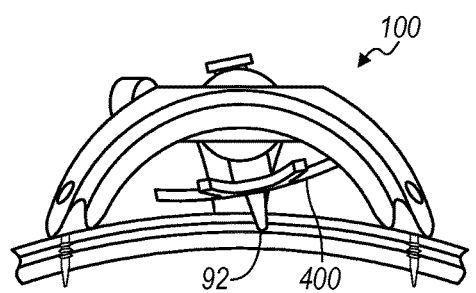
Figures 2, 3, 4, 5:
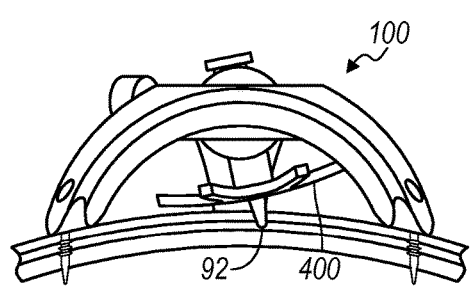

The stereotactic access device may further include a locking and/or fixing feature for reversibly locking the orientation and/or position of the mounting and/or guiding feature relative to the stereotactic access device, as shown with the thumbscrew 112 in FIGS. 1B and 1C, and with the screws 112 in FIGS. 5, 5A and 5B. For example, at least one securing screw may be utilized to frictionally contact and/or at least partially screw into a mounting and/or guiding feature to lock its position and/or orientation. Also for example, at least two securing screws may be utilized with mounting and/or guiding features having multiple degrees of freedom to aid in preventing loss of alignment and orientation, such as by each locking a particular axis of rotation, as illustrated with the two screws 112 in FIGS. 5, 5A and 5B.

Figure 9:
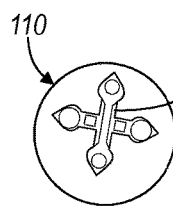
FIGS. 9, 9A, 9B and 9C illustrate examples of different channels and apertures in a mounting ball.
Figure 9A:
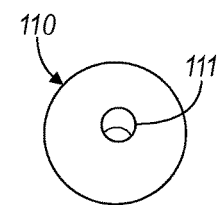
Figure 9B:
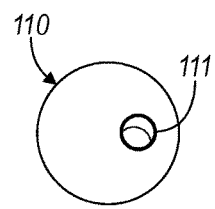
Figure 9C:
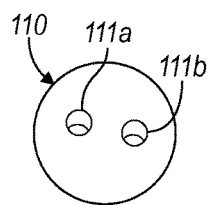

The mounting and/or guiding feature may include a variety of channels and/or other apertures, examples of which are illustrated in FIGS. 9, 9A, 9B and 9C. In some embodiments, the mounting and/or guiding feature, such as the sphere 110 as illustrated, may include a centered channel 111, as in FIG. 9A, and in other embodiments, the mounting and/or guiding feature may include an off-center channel and/or multiple channels such that a greater degree of variability in position and trajectory for guiding a medical device and/or other device through the stereotactic access device may be achieved from a single static mounting of the stereotactic access device onto a patient's body. FIG. 9 illustrates a cross-shaped slot aperture 111' with multiple access positions. FIG. 9B illustrates an off center channel 111. FIG. 9C illustrates multiple channels 111a and 111b. Various other channels and apertures may be utilized depending on a particular application or device being used.

This variability may be desirable as unexpected and/or unplanned obstructions may be present in a planned trajectory to a target and it may generally be desirable to make small adjustments to the trajectory without having to reposition the entire stereotactic access device which may be attached a patient's body.

In a further aspect, a stereotactic access device includes features for aiding in mounting, positioning and/or registering the position and/or orientation of the stereotactic access device, for example, in relation to the patient's body and/or portion thereof. In some embodiments, the stereotactic access device may include, for example, mounting hardware such as, for example, screws, nails, bolts, pins, and/or any other appropriate mounting hardware or combination thereof. For certain curvatures and/or shapes of a body and/or portion thereof, spacers and/or other adjustment accessories, such as spacers between the end of the mounting arm(s) and the body, may be utilized such that a stable plane may be established with the stereotactic access device. In general, the mounting hardware may provide, for example, stable and/or secure retention and/or fixation of the stereotactic access device to a patient's body and/or portion thereof, such as, for example, to a bone or soft tissue via, for example, mounting arms. In some embodiments, the mounting hardware may also provide and/or act as, for example, fiducial markers for aiding in positioning and/or registering the position and/or orientation of the stereotactic access device, such as, for example, relative to the patient's body and/or portion thereof. For example, the mounting hardware may be registered and/or imaged by a detection modality, such as, for example, magnetic resonance imaging (MRI), X-ray, computerized tomography (CT), ultrasound, and/or any other appropriate detection modality or combination thereof.

As illustrated in FIG. 1, the stereotactic access device 100 may include, for example, screws 103, which may be mounted at the ends 104 of the mounting arms 102. The screws 103 may be, for example, self-tapping such that they may, for example, thread themselves into a surface, such as the patient's body. The screws 103 may also act as fiducials, as discussed above. For certain curvatures of the body and/or other situations requiring adjustment of the apparent dimensions of the mounting arms 102, spacers may be included, such as, for example, about the screws 103 between the end of the mounting arms 102 and the body, such that they may, for further example, effectively lengthen the mounting arms 102.

In another aspect, a stereotactic access device is utilized in methods for accessing the interior of a patient's body at a particular location and/or along a particular trajectory. In an exemplary embodiment, a method for stereotactic access may include:

Step 1: As illustrated in FIG. 2-1, after registration of the patient and navigation tools, a standard navigation wand 200 may be used to determine and mark a rough entry point 92 on the patient's body 90, and the patient may then be prepped. The navigation wand 200 may then be inserted into the sphere of the stereotactic access device 100 such that the surgeon may hold both devices, for example, with one hand. Examples of a navigation system and registration are set forth in U.S. Pat. Nos. 6,491,699 and 7,313,430, which are hereby incorporated by reference herein.

Step 2: As illustrated in FIG. 2-2, using stereotactic navigation software, the surgeon may find the desired entry point 92 again and may then align the navigation wand 200 with the planned trajectory to a target. The surgeon may then slide the stereotactic access device 100 down onto the patient's body 90 and mounting hardware, such as, for example, three small titanium screws, may then be secured, for example, through the skin and into bone, such as, for example, the skull. The navigation wand 200 may be used again to confirm the trajectory, such as prior to locking the stereotactic access device 100 in place.

Step 3: As illustrated in FIG. 2-3, the surgeon may then remove the navigation wand 200 and replace it with, for example, one of several various sized drill adapters 310. A stab incision may also be made at the entry site 92 under the stereotactic access device 100. A surgical drill 300 may then be inserted along the locked trajectory and a twist drill hole may be created through, for example, a bone such as the skull, at the entry site 92.

Step 4: As illustrated in FIG. 2-4, the drill adapter 310 may then be retracted to optionally allow, for example, a bone screw or anchor 400 to be placed under the stereotactic access device 100. The drill adapter 310 may be made to fit into the bone screw or anchor's 400 proximal end such that the threads of the screw 400 may fall into the hole created in step 3 at the entry site 92. A biopsy probe may also be passed directly through an appropriate adapter, for example, such as with its own thumb screw, and may be used to acquire, for example, tissue samples.

Step 5: As illustrated in FIG. 2-5, for placement of probes or electrodes, the surgeon may secure the bone screw 400 by securing it in, for example, the previously drilled hole at the entry site 92.

Step 6: As illustrated in FIG. 2-6, the stereotactic access device 100 may be removed, for example, by unscrewing the three screws, and if any stab incisions were created, they may be closed using a single staple or suture. A Touhy-Borst adapter 410 may also be threaded onto the proximal female luer of the bone screw 400, which may allow applicators to pass through while ensuring a sterile field.

In some embodiments, the stereotactic access device 100 may also be left in place after a hole at entry site 92 is drilled. For example, a bone screw 400 may connect to the stereotactic access device 100 such that a continuous sealed channel may be established from the stereotactic access device 100 through the bone screw 400 and into the body 90. A sealing cap and/or other sealing component may also be included to close off the introducing end of the stereotactic access device 100.

Figure 4:
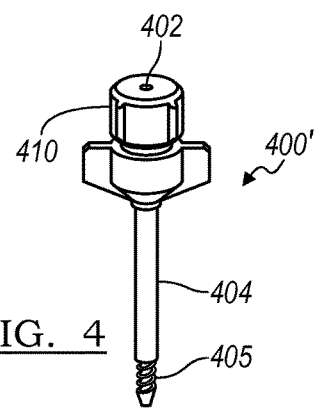
Figure 4A:
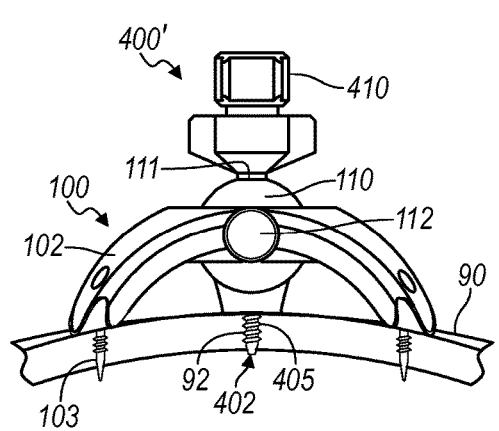
Figure 4B:
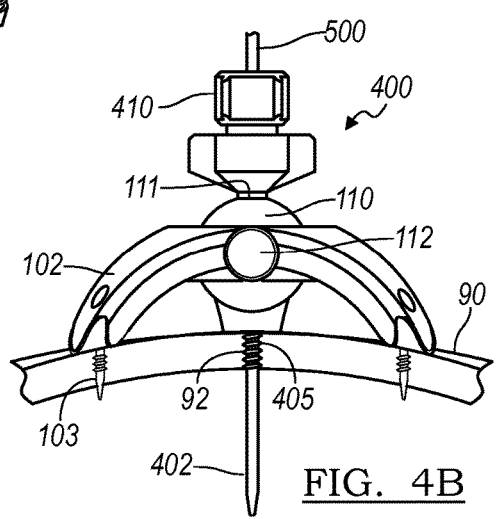

In other embodiments, such as illustrated in FIGS. 4, 4A and 4B, the stereotactic access device 100 may be left in place and an introducer 400' may be inserted into the channel 111 of the stereotactic access device 100 and into the drilled hole at the entry site 92 in the body 90. The end of the introducer 400' may further include a cap and/or a seal, such as the sealing cap 410 as illustrated in FIG. 4, such that the channel 402 may be kept sterile. The insertable portion 404 may be retained in the guide channel 111. The insertable end 405 may further be threaded to engage the drilled hole at the entry site 92. A device 500, such as a laser probe and/or other type of medical device, may then be inserted into the channel 402 through the introducer 400' and into the body through the entry site 92, as illustrated in FIG. 4B.

Figures 2, 3, 4, 5, 6:
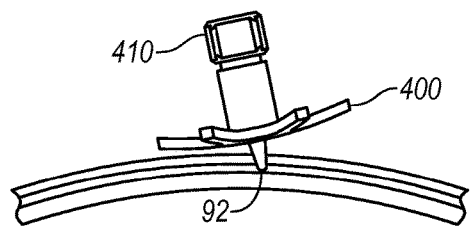
Figure 3:
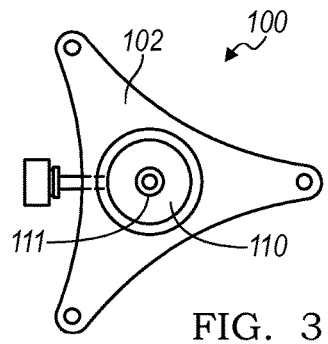
Figure 3A:
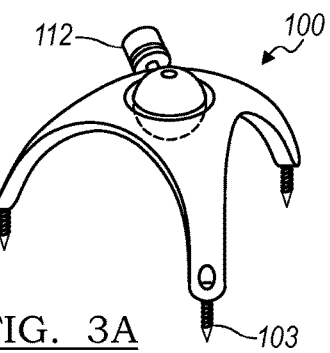
Figure 3B:
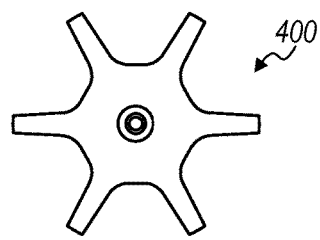
FIGS. 3B and 3C illustrate an example of a bone anchor for use with a frameless stereotactic access device.
Figure 3C:
Figure 5C:
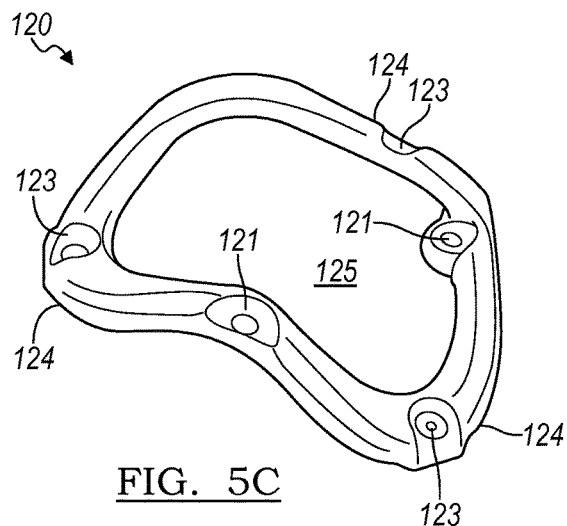
FIGS. 5C and 5D illustrate the frame portion of a frameless stereotactic access device.
Figure 5D:
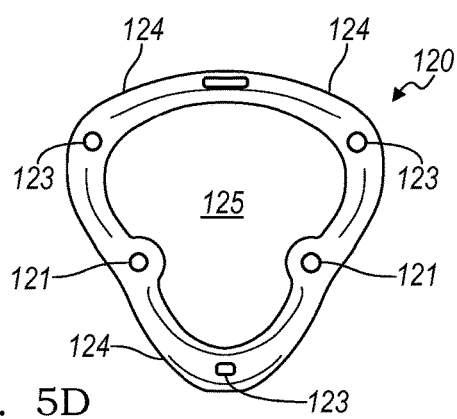

In an exemplary aspect, a stereotactic access device may be a multiple part device which may, for example, be utilized to aid in maintaining a sterile field for use in stereotactic surgery while establishing a trajectory to a target inside a patient's body. In one exemplary embodiment, as illustrated in FIGS. 5, 5A and 5B, the stereotactic access device 100' may include a frame portion 120 and an attachable/detachable cover portion 102'. As with the stereotactic access device 100, above, the stereotactic access device 100' may generally form a tripod to accommodate curved and/or uneven surfaces, as explained above, with ends 104 of the cover portion 102' and the corresponding ends 124 of the frame portion 120. The frame portion 120 may generally form an opening 125, as shown in FIGS. 5C and 5D, which may be covered by the cover portion 102' when it is attached. In general, the frame portion 120 may be secured to the patient's body 90, such as on a curved and/or other non-flat surface 92, as shown in FIG. 6, while the cover portion 102' may be attached and removed from the frame portion 120, as shown in FIG. 6A, such that the stereotactic access device 100' as a whole may be secured to the patient's body 90. This may be desirable as the stereotactic procedures may take place partially in a sterile environment, such as an operating room, and partially in an unsterile environment, such as a medical imaging room or suite. Thus, prior to performing a stereotactic surgical procedure, the stereotactic access device 100' may be oriented and attached to a patient's body 90 in an unsterile environment using the frame portion 120 and an unsterile cover portion 102', followed by removal of the unsterile cover portion 102' and replacement with a sterile cover portion 102' for use in a sterile environment. A kit may be provided with multiple cover portions 102' for use in this way. The cover portions 102' may further be visually and/or materially different for each purpose. For example, a non-sterile cover portion 102' may not require a material that may withstand significant sterilization.

In some embodiments, the cover portion 102', the frame portion 120, and/or the entire stereotactic access device 100 or 100', or components or portions thereof, may be translucent or transparent to aid in, for example, visualizing the position, orientation of the stereotactic access device 100 or 100' and/or the patient's body 90 underneath.

In some embodiments, as illustrated in FIGS. 5, 5A, 5B, 5C and 5D, mounting hardware, such as the screws 103 shown, may insert into the frame portion 120 at mounting holes 123 at each end 124 to secure the frame portion 120 to a patient's body 90. Further, the cover portion 102' may include apertures 104a at each end 104 to provide access to the screws 103 through the cover portion 102' while it is attached to the frame portion 120. This may be utilized, for example, to manipulate the screws 103 while the cover portion 102' is attached to the frame portion 120. In general, the mounting hardware, such as the screws 103, may only secure the frame portion 120 to the patient's body 90, and not secure the cover portion 102' to the patient's body 90 directly such that the cover portion 102' may be freely removed and/or attached from the frame portion 120 without disturbing the secured attachment of the frame portion 120 to the patient's body 90.

In some embodiments, the cover portion(s) 102' may also include additional fiducial markers, such as shown with fiducial markers 105, as discussed above, such that they may aid in providing additional registration information and may also be used to verify proper alignment and attachment of the cover portion(s) 102' to the frame portion 120 as they are removable.

FIG. 5' further illustrates an embodiment of a stereotactic access device 100" which may also include a cover portion 102' and a frame portion 120, as above with stereotactic access device 100', and may employ a single securing screw 112 for the mounting ball 110.

In some embodiments, the cover portion(s) 102' and the frame portion 120 may include features for reversible secure attachment to each other, which may include, but are not limited to, screws, nuts, bolts, nails, magnets, reversible adhesives, locking levers, and/or any other appropriate reversible secure attachments.

Figure 5E:
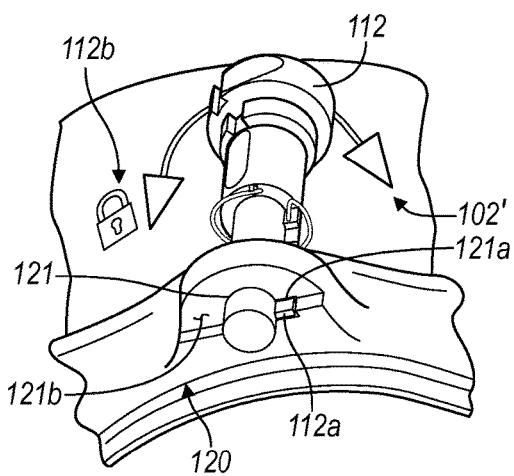
FIGS. 5E and 5F illustrate locking levers for securing a cover portion to a frame portion.
Figure 5F:
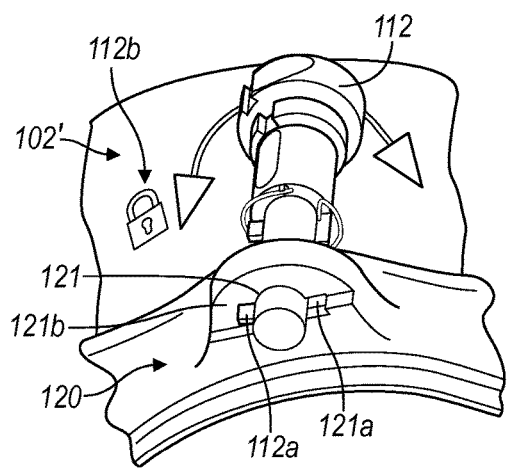

FIGS. 5, 5A, 5B, 5C and 5D illustrate a pair of locking levers 112 which may be used to reversibly secure the cover portion 102' to the frame portion 120. For example and as illustrated, the locking levers 112 may be turned from locked to unlocked (and vice versa) which may manipulate the orientation of locking portion 122a which may secure to the frame portion 120 at locking apertures 121. For example, as shown in FIGS. 5E and 5F, the locking levers 112 may include an extension 112a which may fit through a corresponding shaped portion 121a of aperture 121 of the frame portion 120. Thus, as in FIG. 5E, when the extension 112a is aligned with the portion 121a, the cover 102' may be unlocked from the frame portion 120 and removed. The locking lever 112 may be rotated such that the portion 121a is not aligned with the extension 112a which may abut against the portion 121b to lock the cover portion 102' to the frame portion 120. The cover portion 102' may further include indicators 112b for indicating locked vs. unlocked orientations of the locking levers 112. In general, multiple locking features may be used to aid in ensuring the proper orientation of the cover portion 102' relative to the frame portion 120, as shown with the two locking levers 112 and corresponding features illustrated in FIGS. 5, 5A, 5B, 5C and 5D.

Example of Construction of a Frameless Stereotratic Cranial Access Guide

In an example of a stereotactic access device, a frameless stereotactic cranial access guide (FIGS. 3, 3A, 3B and 3C) includes 2 parts—Tripod 100 and a bone screw 400. The tripod 100 (measuring for example 2.5" in diameter and 1.25" in height) may hold several adapters for various navigation wands, drills, and bone screws 400 (measuring for example 1.5" in diameter). Wherever the tripod 100 is located on the cranium, the feet may be seated to allow all three screws to have a solid hold to the skull, due to the planar tripod body design. Space is provided between the patient's skull and the base of the sphere 110 to allow access to the incision/entry point. The sphere 110 press fits into the body of the tripod 100 and swivels in all directions. The through hole 111 in the sphere 110 may fit various adapters for several parts of the procedure. The thumbscrew 112 is used to tighten and secure the sphere 110 in a particular orientation once the desired trajectory is achieved. Three guide screws 103 are located on the tips 102 of the tripod 100 and may secure to the skull and anchor the guide in its position over the skull, such as, for example, over the entry point.

Example of Orienting and Securing a Stereotactic Access Device to a Patient's Body As illustrated in FIGS. 7 and 7A, a navigation wand 200 may be inserted into the channel 111 of a stereotactic access device 100' and slid down.

As illustrated in FIG. 8, the tip portion 202 of the navigation wand 200 may be contacted with the patient's body 90 at an entry point. The navigation wand 200 may be oriented along a proper trajectory using navigation software and/or imaging.

The stereotactic access device 100' may then be slid down along the tip portion 202 to contact the patient's body 90, as shown in FIG. 8A. The stereotactic access device 100' may be rotated about the navigation wand 200, to, for example, ensure the screws 103 are located at safe entry locations on the patient's body 90 and to ensure that all features of the stereotactic access device 100' are accessible, as illustrated in FIG. 8B.

Figure 8C:
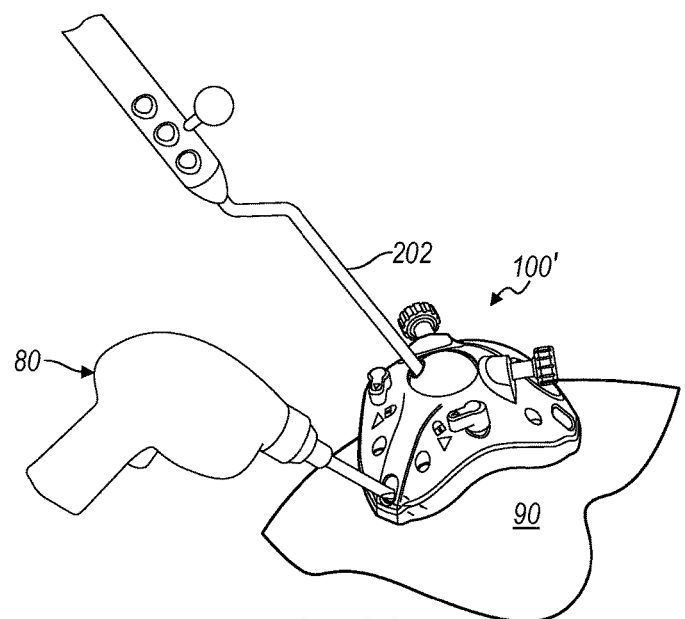
Figure 8D:
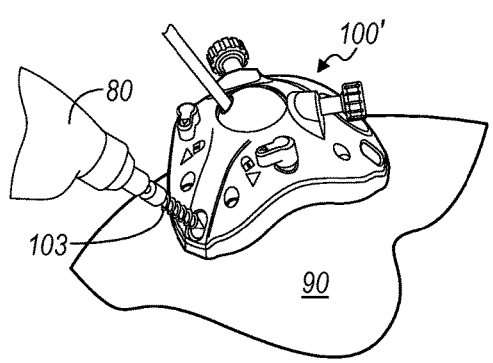
Figure 8E:
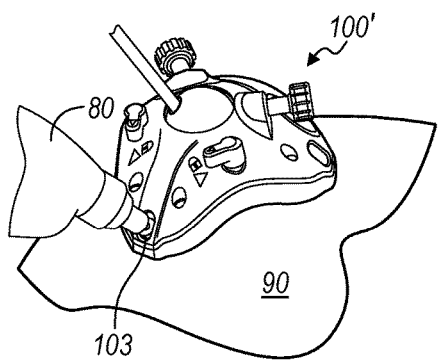

The stereotactic access device 100' may then be secured to the patient's body 90, such as with a screw driver 80 as illustrated in FIGS. 8C, 8D and 8E. The alignment and position of the stereotactic access device 100' may be verified after securing each screw 103. The screws 103 may be secured until the stereotactic access device 100' is sufficiently secure and the attachment to the patient's body 90 is stable and/or rigid.

The stereotactic access device 100' may then be imaged and/or scanned to register its position and alignment relative to the patient's body 90. To move into a sterile environment, the non-sterile cover portion 102' may be removed and the frame portion 120 may be sterilized. A sterile cover portion 102' may then be attached to the frame portion in the same orientation as the non-sterile cover portion 102' and verified for proper alignment and/or position.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A stereotactic access device comprising:
a frame body having an opening therethrough and plurality of mounting ends, each of said mounting ends configured to receive a securing device at an end;
a cover body being attachable and detachable to said frame body, said cover body covering said opening in said frame body when attached; and
a mounting guide having a guide channel, said mounting guide being retained in said cover body;
wherein said plurality of mounting ends forms a stable planar platform with a space underneath said frame body which accommodates curvature of a surface;
wherein the cover body includes apertures to provide access to each securing device at each mounting end, wherein the cover body substantially covers the entire frame body except for the apertures.

2. The stereotactic access device of claim 1, wherein said plurality of mounting ends comprise three ends.

3. The stereotactic access device of claim 1, wherein said securing device comprises a self-tapping screw.

4. The stereotactic access device of claim 3, wherein said self-tapping screw comprises a registerable fiducial.

5. The stereotactic access device of claim 2, wherein said three ends form a tripod.

6. The stereotactic access device of claim 1, wherein said mounting guide comprises a mounting ball.

7. The stereotactic access device of claim 6, further comprising at least one locking screw adapted to reversibly lock said mounting ball in an orientation relative to said cover body.

8. The stereotactic access device of claim 1, further comprising spacers at said mounting ends.

9. A method for stereotactic access to a patient's body comprising:
registering a patient's body and at least one navigation tool in a space utilizing a detection modality;
inserting said navigation tool in a guide channel of a stereotactic access device having a plurality of mounting ends, a plurality of securing screws and at least one locking screw;
aligning said navigation tool relative to said patient's body along a trajectory toward a target;
sliding said stereotactic access device along said trajectory toward said patient's body;
securing said stereotactic access device to said patient's body utilizing said securing screws;
removing said navigation tool;

removing a cover portion of said stereotactic access device while leaving a frame portion attached to said patient's body;

sterilizing said frame portion and at least a portion of said patient's body adjacent to said frame portion;

attaching a sterile cover portion to said frame portion;

inserting a drill through said guide channel;

aligning said drill to said trajectory and locking said guide channel in place utilizing said at least one locking screw; and accessing said patient's body by drilling along said trajectory through said guide channel to form an access channel in said patient's body.

10. The method of claim 9, further comprising placing a bone screw in said access channel.

11. The method of claim 9, further comprising utilizing navigation software to align said navigation tool.

12. The method of claim 9, wherein said access channel is through a skull.

13. The method of claim 9, further comprising inserting an adapter in said guide channel for said drill.

14. The method of claim 10, further comprising removing said stereotactic access device after placing said bone screw.

15. The method of claim 9, further comprising placing an introducer having a through-channel through said guide channel and into said access channel.

16. A system for stereotactic access to a body comprising:
a stereotactic access device comprising:
a frame body having an opening therethrough and a plurality of mounting ends, each of said mounting ends configured to receive a securing device at an end;
a cover body being attachable and detachable to said frame body, said cover body covering said opening in said frame body when attached;
a mounting ball having a guide channel, said mounting ball being retained in said cover body; and
at least one locking screw adapted to reversibly lock said mounting ball in an orientation relative to said body, the at least one locking screw includes a pointed distal tip configured to screw into said mounting ball;
wherein said plurality of mounting ends forms a stable planar platform with an access space; and
a bone screw having a threaded portion and a channel.

17. The system of claim 16, wherein said bone screw comprises an introducer adapted to be received in and through said guide channel.

18. The system of claim 17, further comprising a sealing cap on said introducer.

19. A stereotactic access device comprising:
a frame body having an opening therethrough and plurality of mounting ends, each of said mounting ends configured to receive a securing device at an end;
a cover body being attachable and detachable to said frame body, said cover body covering said opening in said frame body when attached; and
a mounting ball having a guide channel, said mounting ball being retained in said cover body;
wherein said plurality of mounting ends forms a stable planar platform with a space underneath said frame body which accommodates curvature of a surface;
wherein said guide channel includes a plurality of guide channels extending through the mounting ball.

20. The system of claim 19, further comprising at least one locking screw adapted to reversibly lock said mounting ball in an orientation relative to said body.

21. The system of claim 20, wherein the at least one locking screw includes a pointed distal tip configured to screw into said mounting.

22. The stereotactic access device of claim 19, wherein at least one of said plurality of guide channels is an off-center guide channel.

23. A stereotactic access device comprising:
a frame body having an opening therethrough and plurality of mounting ends, each of said mounting ends configured to receive a securing device at an end;
a cover body being attachable and detachable to said frame body, said cover body covering said opening in said frame body when attached; and
a mounting guide having a guide channel, said mounting guide being retained in said cover body;
wherein said plurality of mounting ends forms a stable planar platform with a space underneath said frame body which accommodates curvature of a surface;
wherein said guide channel is a cross-shaped slot aperture defining multiple access positions.

24. A stereotactic access device comprising:
a frame body having an opening therethrough and plurality of mounting ends, each of said mounting ends configured to receive a securing device at an end;
a cover body being attachable and detachable to said frame body, said cover body covering said opening in said frame body when attached; and
a mounting guide having a guide channel, said mounting guide being retained in said cover body;
wherein said plurality of mounting ends forms a stable planar platform with a space underneath said frame body which accommodates curvature of a surface;
wherein said cover body includes a first cover body and a second cover body, wherein the first cover body is configured to be a non-sterile cover body and the second cover body is configured to be a sterile cover body.

25. A stereotactic access device comprising:
a frame body having an opening therethrough and plurality of mounting ends, each of said mounting ends configured to receive a securing device at an end;
a cover body being attachable and detachable to said frame body, said cover body covering said opening in said frame body when attached; and
a mounting guide having a guide channel, said mounting guide being retained in said cover body;
wherein said plurality of mounting ends forms a stable planar platform with a space underneath said frame body which accommodates curvature of a surface;
wherein portions of the stereotactic access device are formed to be translucent to assist in visualizing the position or orientation of the stereotactic access device.

26. The stereotactic access device of claim 25, wherein the cover body includes apertures to provide access to each securing device at each mounting end, wherein the cover body substantially covers the entire frame body except for the apertures.

27. A stereotactic access device comprising:
a frame body having an opening therethrough and plurality of mounting ends, each of said mounting ends configured to receive a securing device at an end;
a cover body being attachable and detachable to said frame body, said cover body covering said opening in said frame body when attached; and
a mounting guide having a guide channel, said mounting guide being retained in said cover body;

wherein said plurality of mounting ends forms a stable planar platform with a space underneath said frame body which accommodates curvature of a surface;

wherein the cover body includes a plurality of fiducial markers used to verify proper alignment and attachment of the cover body to the frame body.

28. A stereotactic access device comprising:

a frame body having an opening therethrough and plurality of mounting ends, each of said mounting ends configured to receive a securing device at an end;

a cover body being attachable and detachable to said frame body, said cover body covering said opening in said frame body when attached;

a mounting guide having a guide channel, said mounting guide being retained in said cover body; and a locking lever extending through the cover body to reversibly secure the cover body to the frame body upon manipulating the orientation of the locking lever;

wherein said plurality of mounting ends forms a stable planar platform with a space underneath said frame body which accommodates curvature of a surface.

* * * * *

UNITED STATES PATENT AND TRADEMARK OFFICE
CERTIFICATE OF CORRECTION

| | |
|---|---|
| PATENT NO. | : 9,901,400 B2 |
| APPLICATION NO. | : 14/602591 |
| DATED | : February 27, 2018 |
| INVENTOR(S) | : Gowda et al. |

Page 1 of 1

It is certified that error appears in the above-identified patent and that said Letters Patent is hereby corrected as shown below:

On the Title Page

Column 1, Line 1, (73) Assignee please delete "Visualise, Inc.," and insert --Visualase, Inc.,-- therefore Signed and Sealed this
Fifth Day of March, 2019

Andrei Iancu
*Director of the United States Patent and Trademark Office*